United States Patent [19]

Scholz et al.

[11] Patent Number: 5,354,259
[45] Date of Patent: Oct. 11, 1994

[54] MICROFIBER FILLERS FOR ORTHOPEDIC CASTING TAPES

[75] Inventors: Matthew T. Scholz, Woodbury; Worku A. Mindaye, Cottage Grove, both of Minn.

[73] Assignee: Minnesota Mining and Manufacturing Company, St. Paul, Minn.

[21] Appl. No.: 8,755

[22] Filed: Jan. 25, 1993

[51] Int. Cl.⁵ .................. A61F 5/01; A61L 15/08; A61L 15/10; A61L 15/12; A61L 15/14

[52] U.S. Cl. ................................ 602/8; 427/180; 427/203; 427/341; 428/240; 428/241; 428/242; 428/244

[58] Field of Search ............... 602/8; 428/241, 242, 428/244, 240; 427/180, 203, 341

[56] References Cited

U.S. PATENT DOCUMENTS

| | | | |
|---|---|---|---|
| 2,765,513 | 10/1956 | Walton | 26/18.6 |
| 3,077,655 | 2/1963 | Runton | 26/18.5 |
| 3,630,194 | 12/1971 | Boardman . | |
| 3,908,644 | 9/1975 | Neinart et al. . | |
| 3,932,526 | 1/1976 | Koshar . | |
| 3,972,323 | 8/1976 | Boricheski . | |
| 4,041,581 | 8/1977 | Diggle, Jr. | 26/18.6 |
| 4,084,982 | 4/1978 | Prior et al. | 106/105 |
| 4,131,114 | 12/1978 | Kirkpatrick et al. . | |
| 4,411,262 | 10/1983 | von Bonin et al. . | |
| 4,473,671 | 9/1984 | Green | 523/105 |
| 4,502,479 | 3/1985 | Garwood et al. . | |
| 4,609,578 | 9/1986 | Reed | 428/76 |
| 4,667,661 | 5/1987 | Scholz et al. . | |
| 4,668,563 | 5/1987 | Buese et al. | 428/230 |
| 4,705,840 | 11/1987 | Buckanin | 528/53 |
| 4,841,958 | 6/1989 | Ersfeld et al. . | |
| 4,940,047 | 7/1990 | Richter et al. . | |
| 4,947,839 | 8/1990 | Clark et al. . | |
| 4,984,566 | 1/1991 | Sekine et al. . | |
| 5,014,403 | 5/1991 | Buese | 28/170 |

FOREIGN PATENT DOCUMENTS

0355635  2/1990  European Pat. Off. .
0407056  6/1990  European Pat. Off. .

Primary Examiner—James C. Cannon
Attorney, Agent, or Firm—Gary L. Griswold; Walter N. Kirn; F. Andrew Ubel

[57] ABSTRACT

The present invention provides an article, comprising: a fabric sheet; a curable resin coated onto the fabric sheet; and a plurality of microfiber fillers dispersed into the resin. The incorporation of microfiber fillers into the casting materials of the present invention adds substantially to the strength of the cured casting material, particularly when the fabric used therein is a non-fiberglass fabric, while not detracting from the handling properties of the uncured casting tape or bandage.

The microfiber fillers useful in this invention are generally characterized as being short fibers having an aspect ratio greater than five to one. Blends of microfibers having different aspect ratios may be utilized in the casting tapes of the present invention. Preferred microfiber fillers or blends have an aspect ratio between 5:1 and 200:1, more preferably, the aspect ratio of the microfiber is between 5:1 and 50:1, and most preferably, the aspect ratio of the microfiber is between 10:1 and 30:1.

35 Claims, No Drawings

MICROFIBER FILLERS FOR ORTHOPEDIC CASTING TAPES

FIELD OF THE INVENTION

This invention relates to sheet materials coated with a curable polymeric resin. More particularly, this invention relates to a curable resin coated sheet material useful in preparing an orthopedic bandage.

BACKGROUND OF THE INVENTION

Many different orthopedic casting materials have been developed for use in the immobilization of broken or otherwise injured body limbs. Some of the first casting materials developed for this purpose involve the use of plaster of Paris bandages consisting of a mesh fabric (e.g., cotton gauze) with plaster incorporated into the openings and onto the surface of the mesh fabric.

Plaster of Paris casts, however, have a number of attendant disadvantages, including a low strength-to-weight ratio, resulting in a finished cast which is very heavy and bulky. Furthermore, plaster of Paris casts typically disintegrate in water, thus making it necessary to avoid bathing, showering, or other activities involving contact with water. In addition, plaster of Paris casts are not air permeable, and thus do not allow for the circulation of air beneath the cast which greatly facilitates the evaporation and removal of moisture trapped between cast and skin. This often leads to skin maceration, irritation, or infection. Such disadvantages, as well as others, stimulated research in the orthopedic casting art for casting materials having improved properties over plaster of Paris.

A significant advancement in the art was achieved when polyisocyanate prepolymers were found to be useful in formulating a resin for orthopedic casting materials, as disclosed, for example, in U.S. Pat. No. 4,502,479 (Garwood et al.) and U.S. Pat. No. 4,441,262 (Von Bonin et al.). U.S. Pat. No. 4,502,479 sets forth an orthopedic casting material comprising a knit fabric which is made from a high modulus fiber (e.g., fiberglass) impregnated with a polyisocyanate prepolymer resin such as polyurethane. Orthopedic casting materials made in accordance with U.S. Pat. No. 4,502,479 provide significant advancement over the plaster of Paris orthopedic casts, including a higher strength-to-weight ratio and greater air permeability. However, such orthopedic casting materials tend not to permit tactile manipulation or palpation of the fine bone structure beneath the cast to the extent possible when applying a plaster of Paris cast. In this regard, knit fiberglass materials are not as compressible as plaster, and tend to mask the fine structure of the bone as the cast is applied, e.g., the care provider may be limited in "feeling" the bone during reduction of the fracture. Although fiberglass fabrics are somewhat radiolucent they sometimes tend to mask the underlying bone structure to x-ray penetration. Oftentimes a fine mesh or a "shadow" can be seen on the x-ray image. This mesh, corresponding to the knitted fiberglass backing, obstructs the penetration of the x-rays and thereby obscures the fine detail of the underlying bone on the x-ray image.

Fiberglass backings have further disadvantages. Most, if not all, commercially available fiberglass casting bandages are comprised of filaments with diameters much larger than 3.5 microns ($\mu m$). While 3.5 $\mu m$ fibers are considered by the scientific community to be non-respirable, there exists a sizable number of customers that have become concerned about the inhalation of fiberglass dust generated during east removal. Moreover, orthopedic casting materials involving knit fabrics such as fiberglass are somewhat expensive, and may be cost prohibitive for some users.

An example of an orthopedic bandage using a polyester fabric which is not a knitted fabric is disclosed in U.S. Pat. No. 3,972,323 (Boricheski). However, the orthopedic bandage disclosed in U.S. Pat. No. 3,972,323 involves the use of plaster of Paris, and thus is subject to the disadvantages outlined hereinabove for plaster of Paris orthopedic casts, including an inferior strength-to-weight ratio and poor air permeability. A second example of an orthopedic bandage using a polyester fabric which is not a knitted fabric is disclosed in U.S. Pat. No. 4,841,958 (Ersfeld et al.). However, the polyester fabric backing disclosed in U.S. Pat. No. 4,841,958 causes the cast to have a somewhat lower strength and a lower rigidity than fiberglass casts. As such, these casting materials require more layers of casting tape to achieve a weight bearing orthopedic cast.

A cast material comprising a filled thermoplastic crystalline solid polyurethane is disclosed in U.S. Pat. No. 4,473,67 1 (Green). In use, the orthopedic cast material is warmed into a sufficiently high temperature to cause the polymer therein to become soft enough to deform. The orthopedic cast material is molded to conform to the surface shape of the effected portion of the body and then is cooled to room temperature. The filler of the casting material comprises a blend of 20% to 60% by weight of calcium metasilicate fibers and from 40% to 80% by weight silica particles. There are many inherent disadvantages with thermoplastic casting tapes including: (1) a separate heat source is required to cause the polymer to soften; (2) the "set" time is difficult to control due to variable initial and ambient temperatures; and (3) the cast material is prone to undesirable softening if warmed by the user.

From the foregoing, it will be appreciated that what is needed in the an is an orthopedic casting material which has both the advantages of plaster of Paris, e.g., good moldability and palpability of the fine bone structure, and the advantages of non-plaster of Paris materials, e.g., good strength-to-weight ratio and good air permeability. In this regard it would be a significant advancement in the art to provide such a combination of advantages without actually using plaster of Paris, thereby avoiding the inherent disadvantages of plaster of Paris outlined herein. It would be a further advancement in the art to provide such non-plaster of Paris orthopedic casting materials which have as good or better properties than the orthopedic casting materials of the prior art, and which can be made to be significantly less expensive, and therefore less cost prohibitive, than prior art orthopedic casting materials employing knitted fabrics such as fiberglass knits. Such orthopedic casting materials and methods for preparing the same are disclosed and claimed herein.

RELATED APPLICATIONS

Of related interest are the following U.S. patent applications, filed on Jan. 25, 1993 by the assignee of this invention: Microcreping of Fabrics for Orthopedic Casting Tapes—08/008,751; Mechanically Compacted Fabrics for Orthopedic Casting Tapes—08/008,761; Water Curable Resin Compositions—08/008,743; Orthopedic Support Materials and Method—08/008,678;

and Fabric Backing for Orthopedic Support Materials—08/009,923 which are herein incorporated by reference.

SUMMARY OF THE INVENTION

The present invention provides an article, comprising: a fabric sheet; a curable liquid resin coated onto the fabric sheet; and a microfiber filler associated with, e.g., dispersed into, the resin. The incorporation of microfiber fillers into the casting materials of the present invention adds substantially to the strength of the cured casting material, particularly when the fabric used therein is a non-fiberglass fabric, while not detracting from the handling properties of the uncured casting tape or bandage. Therefore, the disadvantages of fiberglass backings can be avoided while maintaining the necessary high strength and high rigidity upon cure.

The microfiber fillers of the present invention are particularly useful when used in conjunction with lower modulus, e.g., non-fiberglass, fabrics where it is particularly critical that the resin component of the composite (i.e., the "composite" comprising resin, filler and fabric article) contribute significantly to the overall strength and durability. In casting tapes it is particularly important that the resin not simply bond the layers together but serve as a load bearing component. Conventional resin systems when coated at acceptable resin loadings, i.e., at loadings which do not exceed that amount of resin which can be coated on the fabric and not occlude the pores of the substrate, do not yield the strength properties required for load bearing casting applications when used with lower modulus backings and without significantly increasing the number of layers of casting tape applied. In contrast, the incorporation of the microfiber fillers of the present invention allows the fabrication of high strength casting bandages, with normal numbers of layers, even with low modulus backings.

DETAILED DESCRIPTION OF THE INVENTION

The present invention relates to orthopedic casting materials and methods for preparing and using such orthopedic casting materials, wherein the materials comprise a backing or fabric, preferably a stretchable backing or fabric, which is impregnated with a curable liquid resin comprising a microfiber filler. In particular, the microfiber fillers employed in the present invention have important characteristics and physical properties which allow the fabrics to be resin loaded to the extent needed to provide proper strength as an orthopedic casting material, while providing necessary porosity and radiolucency as well as improved tactile manipulability, moldability, and palpability. At the same time, the orthopedic casting materials of the present invention are relatively inexpensive, thus providing a more economical alternative to the non-plaster of Paris orthopedic casting materials presently known in the art which employ knitted fabrics such as fiberglass fabrics.

One element of this invention is a semi-rigid or flexible sheet upon which a curable resin can be coated to reinforce the sheet when the resin is cured thereon. The sheet is preferably porous such that the sheet is only partially impregnated with the resin. Examples of suitable sheets are non-woven, woven, or knit fabrics comprised of natural or synthetic fibers or materials. The sheet may alternatively be referred to as the "scrim" or the "backing." Although the present invention provides the ability to make high strength casting materials with non-fiberglass backings such as polyester fabrics, there may be instances where one may desire to use a fiberglass backing.

Where fiberglass backings are desired, suitable sheets which may be employed are knit fiberglass fabrics such as disclosed in U.S. Pat. Nos. 4,502,479; 4,609,578; 4,668,563; and 5,014,403 and in U.S. patent application Ser. No. 07/976,402. Particularly preferred sheets of this type are extensible, heat-set fabrics as disclosed in U.S. Pat. No. 4,609,578 (Reed) which is herein incorporated by reference. One example of a knitted fiberglass scrim which is within the scope of U.S. Pat. No. 4,609,578 is known by 3M, St. Paul, Minn., as the Scotchcast TM 2 knitted fiberglass scrim. The Scotchcast TM 2 scrim is used in the manufacture of 3M's Scotchcast TM 2 and Scotchcast TM Plus orthopedic casting materials.

As will be appreciated, the advantages of the present invention are most evident when non-fiberglass backings are used. Suitable non-fiberglass backings of the present invention include fabrics comprising: natural organic fibers; animal derived materials; naturally based organic polymer fibers; and synthetic polymer fibers. Suitable natural organic fibers for use in the fabric of the present invention include: vegetable derived materials such as abaca, cotton, flax, hemp, jute, kapok, linen, ramie, and sisal. Suitable animal derived materials include wool, mohair, vicuna, other animal hairs, and silk. Presently preferred organic fibers include: cotton and wool. Cotton is presently most preferred.

Suitable naturally based organic polymers for use in the fabric of the present invention include: acetate, azlon, rayon, and triacetate. Suitable synthetically prepared organic polymers include: acrylic, aramid, nylon, olefin (e.g., poly(1-butene), polyethylene, poly(3-methyl-1-butene), poly(1-pentene), polypropylene, and polystyrene), polyester, polytetrafluoroethylene, poly(vinyl alcohol), poly(vinyl chloride), and poly(vinylidine chloride). Presently preferred synthetic polymer fibers include: acrylic, nylon, polyethylene, polypropylene, polyester, and rayon. Presently most preferred synthetic polymer fibers include: nylon, polyester, and rayon. In this regard, preferred knitted, woven, or nonwoven sheets made of organic fibers are described, for example, in U.S. Pat. Nos: 4,940,047; 4,984,566; and 4,841,958 (Ersfeld et al.) which are herein incorporated by reference.

Non-fiberglass sheets are preferred over fiberglass sheets although either type of backing may be used in practicing the instant invention. Non-fiberglass sheets are presently believed to benefit to a greater extent from the incorporation of the microfiber filler than casting materials comprising fiberglass sheets. This is believed to be due to the generally lower strength of untilled non-fiberglass orthopedic casting tapes. In addition, the benefit relating to radiolucency is realized when the backing material is non-fiberglass.

The curable resins useful in this invention are resins which can be used to coat a sheet material and which can then be cured to reinforce the sheet material. The resin is curable to a crosslinked thermoset state. The preferred curable resins are fluids, i.e., compositions having viscosities between about 5 Pa s and about 500 Pa s, preferably about 10 Pa s to about 100 Pa s as measured at 23° C. using a Brookfield RVT Rotovisco viscometer.

The resin used in the casting material of the invention is preferably any curable resin which will satisfy the functional requirements of an orthopedic cast. Obviously, the resin must be nontoxic in the sense that it does not give off significant amounts of toxic vapors during curing which may be harmful to either the patient or the person applying the cast and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. Then in a short time following completion of cast application, it should become rigid or, at least, semi-rigid, and strong to support loads and stresses to which the cast is subjected by the activities of the wearer. Thus, the material must undergo a change of state from a fluid-like condition to a solid condition in a matter of minutes.

The preferred resins are those cured with water. Presently preferred are urethane resins cured by the reaction of a polyisocyanate and a polyol such as those disclosed in U.S. Pat. No. 4,131,114. A number of classes of water-curable resins known in the art are suitable, including polyurethanes, cyanoacrylate esters, and, when combined with moisture sensitive catalysts, epoxy resins and prepolymers terminated at their ends with trialkoxy- or trihalo-silane groups. For example, U.S. Pat. No. 3,932,526 discloses that 1,1-bis(perfluoromethylsulfonyl)-2-aryl ethylenes cause epoxy resins containing traces of moisture to become polymerized.

Resin systems other that those which are water-curable may be used, although the use of water to activate the hardening of an orthopedic casting tape is most convenient, safe and familiar to orthopedic surgeons and medical casting personnel. Resin systems such as that disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol) are suitable. The resin is hardened upon wetting with solutions of a tertiary amine and an organic peroxide. Also, the water may contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the an as a redox initiator system). The strength, rigidity and rate of hardening of such a bandage is subjected to the factors disclosed herein.

Some presently more preferred resins for use in the present invention are water-curable, isocyanate-functional prepolymers. Suitable systems of this type are disclosed, for example, in U.S. Pat. No. 4,411,262, and. in U.S. Pat. No. 4,502,479. Presently more preferred resin systems are disclosed in U.S. Pat. No. 4,667,661 and U.S. patent application Ser. No. 07/376,42 1 which is herein incorporated by reference. The following disclosure relates primarily to the preferred embodiment of the invention wherein water-curable isocyanate-functional prepolymers are employed as the curable resin.

It is preferred to coat the resin onto the fabric as a polyisocyanate prepolymer formed by the reaction of an isocyanate and a polyol. It is preferred to use an isocyanate which has low volatility such as diphenylmethane diisocyanate (MDI) rather than a more volatile material such as toluene diisocyanate (TDI). Suitable isocyanates include 2,4-toluene diisocyanate, 2,6-toluene diisocyanate, mixture of these isomers, 4,4'-diphenylmethane diisocyanate, 2,4'-diphenylmethane diisocyanate, mixture of these isomers together with possible small quantities of 2,2'-diphenylmethane diisocyanate (typical of commercially available diphenylmethane diisocyanate), and aromatic polyisocyanates and their mixture such as are derived from phosgenation of the condensation product of aniline and formaldehyde. Typical polyols for use in the prepolymer system include polypropylene ether glycols (available from Arco Chemical under the trade name Arcol TM PPG and from BASF Wyandotte under the trade name Pluracol TM), polytetramethylene ether glycols (Polymeg TM from the Quaker Oats Co.), polycaprolactone diols (Niax TM PCP series of polyols from Union Carbide), and polyester polyols (hydroxyl terminated polyesters obtained from esterification of dicarboxylic acids and diols such as the Rucoflex TM polyols available from Ruco division, Hooker Chemical Co.). By using high molecular weight polyols, the rigidity of the cured resin can be reduced.

An example of a resin useful in the casting material of the invention uses an isocyanate known as Isonate TM 2143L available from the Dow Chemical Company (a mixture of di- and tri-isocyanates containing about 73% of MDI) and a polypropylene oxide polyol from Union Carbide known as Niax TM PPG725. To prolong the shelf life of the material, it is preferred to include from 0.01 to 1.0 percent by weight of benzoyl chloride or another suitable stabilizer.

The reactivity of the resin once it is exposed to the water curing agent can be controlled by the use of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl)ethoxy]ethyl]-morpholine (MEMPE) prepared as described in U.S. Pat. No. 4,705,840, the disclosure of which is incorporated by reference, at a concentration of about 0.05 to about 5 percent by weight.

Foaming of the resin should be minimized since it reduces the porosity of the cast and its overall strength. Foaming occurs because carbon dioxide is released when water reacts with isocyanate groups. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. The most satisfactory method of minimizing foaming is to add a foam suppressor such as silicone Antifoam A (Dow Coming), or Anti-foam 1400 silicone fluid (Dow Coming) to the resin. It is especially preferred to use a silicone liquid such as Dow Coming Antifoam 1400 at a concentration of about 0.05 to 1.0 percent by weight. Water-curable resins containing a stable dispersion of hydrophobic polymeric particles, such as disclosed in U.S. patent application Ser. No. 07/376,421 and laid open as European Published Patent Application EPO 0 407 056, may also be used to reduce foaming.

A water-curable isocyanate-functional prepolymer as used herein means a prepolymer derived from polyisocyanate, preferably aromatic, and a reactive hydrogen compound or oligomer. The prepolymer has sufficient isocyanate-functionality to cure upon exposure to water, e.g., moisture vapor, or preferably liquid water.

Also included as presently more preferred resins in the instant invention are non-isocyanate resins such as water reactive liquid organometallic compounds. These resins are especially preferred as an alternative to isocyanate resin systems. Water-curable resin compositions suitable for use in an orthopedic cast consist of a water-reactive liquid organometallic compound and an organic polymer. The organometallic compound is a compound of the formula $(R^1O)_xMR^2_{(y-x)}$ wherein:- each $R^1$ is independently a $C_1-C_{100}$ hydrocarbon group, optionally interrupted in the backbone by 1-50 nonperoxide —O—, —S—, —C(O)—, or —N— groups; each $R^2$ is independently selected from the group consisting of hydrogen and a $C_1-C_{100}$ hydrocarbon group, optionally interrupted in the backbone by 1-50 nonperoxide —O—, —S—, —C(O)—, or —N— groups; x is an integer between 1 and y, inclusive; y is the valence of M; and M is boron, aluminum, silicon, or titanium. The organic polymer is either an addition polymer or a condensation polymer. Addition polymers are preferably utilized as the organic polymer constituent. Particularly useful addition polymers are those made from ethylenically unsaturated monomers. Commercially available monomers, from which such addition polymers can be formed, include but are not limited to, ethylene, isobutylene, 1-hexene, chlorotrifluoroethylene, vinylidene chloride, butadiene, isoprene, styrene, vinyl napthalene, ethyl acrylate, 2-ethylhexyl acrylate, tetrahydrofurfuryl acrylate, benzyl acrylate, poly(ethylene oxide) monoacrylate, heptafluorobutyl acrylate, acrylic acid, methyl methacrylate, 2-dimethylaminoethyl methacrylate, 3-methacryloxypropyltris(trimethylsiloxy) silane, isobutyl methacrylate, itaconic acid, vinyl acetate, vinyl stearate, N,N-dimethylacrylamide, tert-butyl acrylamide, acrylonitrile, isobutyl vinyl ether, vinyl pyrrolidinone, vinyl azlactone, glycidyl methacrylate, 2-isocyanatoethyl methacrylate, maleic anhydride, vinyl triethoxysilane, vinyl tris(2-methoxyethoxy)silane, and 3-(trimethoxysilyl)propyl methacrylate. Polymers bearing hydrolyzable functionality are preferred. An acidic or basic catalyst may be used to accelerate the water cure of these compositions. Strong acid catalysts are preferred.

The microfiber fillers of the present invention provide many benefits when incorporated into any of the aforementioned resins. For example, resins which incorporate microfiber fillers exhibit: a dramatic increase in strength when coated on a backing (in this regard the increase in strength is dramatic when the filled resin is coated on non-fiberglass backings); an increased "early strength" upon curing; an improved durability and higher modulus; good and often better layer-to-layer lamination strength; a lower exotherm upon setting; and a lower effective resin cost compared to resins which do not incorporate such microfiber fillers. Casting bandages which employ the microfiber fillers and non-fiberglass backings also are presently believed to have improved radiolucency compared to typical fiberglass bandages, i.e., the microfiber fillers do not superimpose a mesh shadow pattern on the image of the bone, thereby obscuring fine details of the bone. In addition, suspensions employing the microfiber fillers of the present invention exhibit generally very little increase in resin viscosity thereby ensuring easy unwind of the casting bandage and good handling properties such as drapability.

A "microfiber filler" as used herein, is a filler which when incorporated into the casting tapes of the present invention provides the desired increase in strength while not adversely affecting the uncured resin suspension viscosity (thereby adversely affecting the drapability of the casting tape). The microfiber fillers useful in this invention are generally characterized as being short fibers having an aspect ratio greater than about five to one. "Aspect ratio" as used herein, refers to the ratio of the fiber's length to its diameter. For fibers having an irregular or non-circular cross section, the "diameter" of the microfiber shall be equal to the largest width across the microfiber. Blends of microfibers having different aspect ratios may be utilized in the casting tapes of the present invention. For purposes of this invention, when blends of microfibers are employed, the aspect ratio of the blend of microfibers refers to the mean aspect ratio. Preferred microfiber fillers or blends have an aspect ratio between 5:1 and 200:1. More preferably, the aspect ratio of the microfiber is between 5:1 and 50:1. Most preferably, the aspect ratio of the microfiber is between 10:1 and 30:1.

Suitable microfibers have a mean diameter between approximately 1 and 60 microns ($\mu$m) and a mean length between approximately 25 and 1000 $\mu$m. Preferred microfiber fillers or blends have a mean diameter between 0.1 and 60 $\mu$m, more preferably, the mean diameter of the microfiber is between 1 and 40 $\mu$m, and most preferably, the mean diameter of the microfiber is between 1 and 30 $\mu$m. Preferred microfiber fillers or blends have a mean length between 25 and 5,000 $\mu$m, more preferably, the mean length of the microfiber is between 30 and 1,000 $\mu$m, and most preferably, the mean length of the microfiber is between 30 and 500 $\mu$m. The presently most preferred filler, Nyad G Wollastokup, is characterized primarily by mesh size. Ninety percent of this material passes through a 200 mesh screen (127×127 $\mu$m hole size). Visual observation of scanning electron microscope "SEM" photos indicates the average fiber diameter to be in the range of 10 to 30 $\mu$m and the average fiber length to be in the range of 200 to 400 $\mu$m.

The microfiber can be naturally occurring inorganic fibers, synthetic inorganic fibers, naturally occurring organic fibers, and synthetic organic fibers. The fiber, if inorganic, can be amorphous, single crystal (e.g., a whisker), polycrystalline, or multiphase. Blends of fibers can be employed if desired.

The various structural features of inorganic fibers reflect the complex interaction of fiber chemistry and fiber formation technique. Amorphous inorganic fibers such as fiberglass and fused silica fibers are manufactured by melt spinning. Although these fibers possess relatively high tensile strength, their modulus is among the lowest of inorganic fibers. On the other hand, single crystal fibers, sometimes referred to by those skilled in the art as "whiskers," are generally chemically pure and highly ordered. This results in strength approaching the theoretical limit, making them the strongest of all fibers.

Whiskers are the ultimate-strength short-fiber material. They are small (being submicron to several microns in diameter), single-crystal fibers with a high degree of crystalline perfection. In general, the smaller the whisker, the greater the perfection. This perfection results from low dislocation density, low void content, low internal and surface imperfections, and no grain boundaries. Whiskers typically have high mechanical properties: for example, a tensile strength between 13 GPa to 32 GPa (10 times that of most conventional fibers), a modulus of 450 GPa to 900 GPa, an elongation of 3 to 4 percent, and an exceptionally high degree of toughness and nonfriability.

Microfibers can be made relatively quickly by low-cost processing techniques, such as precipitation from a supersaturated solution. However, because they are made rapidly and from a liquid they do not possess the purity and crystalline perfection of a true whisker. These fibers are generally polycrystalline fiber bundles with grain boundaries and they often contain voids, dislocations, and crystalline imperfections rarely found in a true whisker. Nevertheless, such microfibers have, in general, much superior properties than the cured matrix resin which surrounds them and are suitable for use in the casting materials of the present invention.

Suitable inorganic microfibers are presently preferred and include, for example, ceramic fibers formed of pure or mixed metal oxides, boron fibers, milled fiberglass, potassium titanate fibers, calcium sulfate fibers (e.g., Franklin Fiber), and processed mineral fibers such as asbestos (i.e., chrysotile or hydrated magnesium silicate), and wollastonite (i.e., calcium metasilicate—$CaSiO_3$). Asbestos, while suitable, is not preferred at the present time because of health considerations. Suitable organic microfibers include, for example, carbon/graphite fibers and aramid fibers.

Franklin Fiber filler is a whisker form of calcium sulfate which differs significantly from typical calcium sulfate fillers. Franklin Fiber filler is made from gypsum using a hydrothermal synthesis. During this process, gypsum is converted to single crystal, microfibers of calcium sulfate hemihydrate. Subsequent dead burning produces the anhydrous form. Notably, for water reactive resin systems, only the anhydrous form of the microfiber filler is suitable as the water of the hemihydrate form, although "bound" and part of the crystal structure, will cause the resin to react prematurely.

Suitable microfiber fillers of the present invention are incorporated into the liquid resin in an amount sufficient to provide the desired increased strength while not adversely affecting the uncured resin suspension viscosity. A suitable amount of a filler in a resin will result in a suspension having a viscosity prior to being cured of less than 500 Pa s as measured at 23° C. using a Brookfield RTV Rotovisco viscometer with either a #6 or #7 spindle (viscosities greater than 100 Pa s should be measured with the #7 spindle). Preferred suspensions have a viscosity prior to being cured of between about 5 and 100 Pa s, more preferably between about 10 and 70 Pa s and most preferably between about 30 and 70 Pa s. While the exact amount of microfiber filler can not be precisely determined owing to factors such as initial resin viscosity, microfiber type, microfiber size and aspect ratio, suitable suspensions for use in the present invention contain up to about 40 percent microfiber filler. Preferred suspensions of resin and microfiber filler contain between about 3 and 35 percent microfiber filler. More preferred suspensions of resin and microfiber filler contain between about 7 and 25 percent microfiber filler. Most preferred suspensions of resin and microfiber filler contain between about 10 and 25 percent microfiber filler.

In an alternative embodiment of the present invention, the microfiber fillers of the present invention may be first coated on, or incorporated into, the scrim and later coated with a liquid resin. It is presently not believed to be essential that the microfiber fillers be first suspended into the resin.

Shelf stability is a major concern with a casting tape, due to the highly reactive nature of the resin. In the case of water activated materials, which are presently preferred, this presents two issues: (1) keeping the product moisture free; and (2) preventing undesirable side reactions from occurring in the pouch. Since curing of resin-coated materials is initiated by contact with water or water vapor, commercial casting products are routinely stored in moisture-proof pouches or containers. Presently preferred pouches are comprised of aluminum foil/polymer laminate constructions. Since many materials such as water-curable orthopedic casting tapes are frequently stored for extended periods of time before use (1–5 years), storage stability is a significant concern. Preferred microfiber filled materials of the present invention are shelf stable in the absence of water over time. Furthermore, the presence of the microfiber filler appears to cause no significant additional increase in viscosity of the resins over time. In the case of isocyanate functional resins, viscosity increases are generally experienced when basic compounds are added to the resin systems. This is presumably due to side reactions in the absence of moisture such as trimerization of isocyanate groups, allophonate formation (reaction of isocyanate with a urethane functionality), and biuret formation (reaction of isocyanate with a urea functionality).

The effect of the microfiber filler on resin stability can be evaluated by preparing a filled resin composition and a control resin without filler, dividing the resins into sealed jars with approximately 200 g/jar, and placing the sealed jars in an oven at 49° C. Individual jars are removed weekly over a 5–8 week period and equilibrated to 25° C. for 3 hours and tested for viscosity on a Brookfield RVT viscometer as described herein. Any viscosity increases which occur over time for the filled and unfilled resins may then be compared. Preferred microfiber fillers show no significant increase in the rate of viscosity rise compared to the unfilled control resin. Note that the jars containing filler must be turned periodically (e.g. daily) to ensure that the filler remains suspended in the resin. Once the resin is coated onto the scrim, no significant settling or migration of the microfiber fillers is experienced, and excellent uniformity is achieved.

If desired, the microfiber fillers may be surface treated using silanes, titanates, zirconates and the like to enhance resin bonding, ease of mixing, and compatibility. The surface treatment may be performed prior to incorporation of the micro fiber into the resin or in-situ, i.e., the surface treatment agent may be incorporated into the suspension for later reaction with the filler.

The following examples are offered to aid in understanding of the present invention and are not to be construed as limiting the scope thereof. Unless otherwise indicated, all pans and percentages are by weight.

EXAMPLES

Example 1

Viscosity of Microfiber Filled Isocyanate Resins

A 3.8 liter (one gallon) glass vessel equipped with a 12.7 cm×2.54 cm×0.318 cm Teflon TM impeller, addition funnel, nitrogen purge line, and thermometer was assembled and purged with nitrogen for 30 minutes to ensure that the entire apparatus was completely dry. The following chemicals were added to the reactor through the addition funnel in order and at 5 minute intervals:

TABLE 1a

| Chemical | Equivalent weight[3] | Weight (g) | Weight (%) |
|---|---|---|---|
| Isonate 2143L (Dow Chemical Co.) | 144.7 | 1729.3 | 57.64 |
| p-Toluenesulfonyl chloride | | 0.9 | 0.03 |
| Antifoam 1400 (Dow Chemical) | | 5.4 | 0.18 |
| Butylated hydroxytoluene ("BHT") | | 14.4 | 0.48 |
| Pluronic F-108 (BASF) | 7250 | 20.0 | 4.00 |
| MEMPE[1] | | 34.5 | 1.15 |
| Arcol PPG-2025 (Arco) | 1019.3 | 627.6 | 20.90 |
| Arcol LG-650 (Arco) | 86.1 | 72.4 | 5.75 |
| Niax E-562[2] | 1729.9 | 295.5 | 9.85 |

[1]"MEMPE" = Morpholinoethylmorpholinoisopropyl ether.
[2]"E-562" = Polymer filled polyol (formerly available from the Union Carbide Corp. and now available from Arco Chemical Co. as Arcol Polyol 24-32).
[3]The combined ingredients provide an NCO to OH ratio of 4.26.

The agitation rate was gradually increased as the viscosity increased. The vessel was temporarily insulated with glass wool, gently heated with a heating mantle, and the temperature of the reaction was allowed to increase to 55° C. The glass wool was removed along with the agitator, thermometer, and addition funnel. The vessel was sealed and the resin was allowed to cool for 24 hours.

Upon completion of the mixing, i.e., as soon as the ingredients had become homogeneous, and while still warm, the resin ("Resin A") was divided into 375 gram aliquots to which varying amounts of Nyad G 10012 were added as set out below in Table 1b. The resin and Nyad mixture was charged to 400 ml insulated jars and shaken vigorously on a shaker for one hour. After shaking the jars were rolled at approximately 20 rpm for 18 hours. Rolling prevents settling of the filler and thereby maintains the mixture as a homogeneous suspension.

The viscosity was then measured using a Brookfield RVT rotovisco viscometer with spindle no. 6 at 10 rpm. The suspension was maintained at 23° C. during the viscosity measurement.

TABLE 1b

| Run # | Resin (grams) | Nyad G (grams) | Weight % of Nyad G | Viscosity, (Pa s) |
|---|---|---|---|---|
| 1 | 375 | 0 | 0 | 37 |
| 2 | 375 | 3.8 | 1 | 36 |
| 3 | 375 | 11.6 | 3 | 33 |
| 4 | 375 | 19.7 | 5 | 29 |
| 5 | 375 | 28.2 | 7 | 30 |
| 6 | 375 | 41.7 | 10 | 30 |

The above procedure was repeated using the ingredients set out below in Table 1c.

TABLE 1c

| Ingredient | Equivalent Weight[3] | Weight (grams) | Weight (%) |
|---|---|---|---|
| Isonate 2143L | 144.2 | 2052.7 | 58.7 |
| Benzoyl chloride | | 1.75 | 0.05 |
| Antifoam 1400 | | 6.3 | 0.18 |
| BHT | | 16.8 | 0.48 |
| Pluronic F-108 | 7250 | 140.0 | 4.0 |
| MEMPE | | 46.2 | 1.32 |
| Arcol ™ PPG-725[1] | 378.3 | 965.0 | 27.6 |

TABLE 1c-continued

| Ingredient | Equivalent Weight[3] | Weight (grams) | Weight (%) |
|---|---|---|---|
| Arcol ™ PPG-425[2] | 212.5 | 271.2 | 5.75 |

[1]"PPG-725" = polypropylene glycol available from Arco Chemical Co.
[2]"PPG-425" = polypropylene glycol available from Arco Chemical Co.
[3]The combined ingredients provide an NCO to OH ratio of 3.7.

To 375 gram aliquots of the above resin ("Resin B") were added varying levels of Nyad G or, as a comparison, a conventional mica filler. The fillers were added to the resin, shaken, and rolled as described previously. Table 1d illustrates the weight of filler added to each 375 gram resin aliquot and the resultant viscosity of the suspension produced.

TABLE 1d

| Run # | Filler | Weight of filler (%) | Weight of filler added (grams) | Viscosity, (Pa s) |
|---|---|---|---|---|
| 1 | None | 0 | 0 | 29.5 |
| 2 | Nyad G | 3 | 11.6 | 28.0 |
| 3 | Nyad G | 5 | 19.7 | 29.0 |
| 4 | Nyad G | 7 | 28.2 | 32.0 |
| 5 | Mica 1 | 5 | 19.7 | 38.0 |
| 6 | Mica | 7 | 28.2 | 42.5 |

1 "Mica" = 100 mesh #88 Alsibronz WG Mica available from Mearl Corporation, Wilmington, Ma.

Example 2

Viscosity in TEOS Resin

A resin composition was prepared by adding 6.25 parts tetraethylorthosilicate ("TEOS" available from Akzo Chemicals Inc.) and 3.75 parts A-151 silane (available from Union Carbide Co.) to a dry nitrogen purged 75 liter reactor and heating the contents to 140° C. A mixture of 13.13 parts isobutyl methacrylate, 1.88 parts A-174 silane (available from Union Carbide Co.), and 0.563 parts O,O-tert-butyl-O-(2-ethylhexyl)-peroxycarbonate (available from Atochem Co.) was slowly pumped into the reactor over a 1.5 hour period. The ingredients were heated an additional 1.5 hours at 140° C. The ingredients were then cooled to 110° C. and an additional 0.094 parts O,O-tert-butyl-O -(2-ethylhexyl)-peroxycarbonate was charged to the vessel. The ingredients were heated at 110° C. for an additional 19 hours, cooled to room temperature and drained.

To individual 200 ml jars was added approximately 180 gm of the above resin (hereinafter referred to as "Resin T") and 3.6 gm methane sulfonic acid catalyst. Care was taken to perform this and the subsequent procedures in a dry environment, i.e., less than about four percent relative humidity. Nyad G 10012 was then added to the resin at varying levels and mixed using a high shear dispersator. After rolling overnight the viscosities of the suspensions were measured as described in Example 1. Table 2a illustrates the results obtained when different amounts of Nyad G were added to the above resin.

TABLE 2a

| Run # | Filler | Weight % of filler | Viscosity, (Pa s) |
|---|---|---|---|
| 1 | Nyad G 10012 | 0 | 62 |
| 2 | Nyad G 10012 | 5 | 61 |
| 3 | Nyad G 10012 | 10 | 72 |
| 4 | Nyad G 10012 | 15 | 75 |

As the above data illustrates, the addition of 15 weight percent filler increased the viscosity of the suspension by only about 21 percent.

Example 3
Viscosity of Various Filled Resins

The fillers of the present invention offer several improvements over conventional inorganic fillers. Surface treated calcium metasilicate microfibers (Nyad G Wollastokup 10012) with aspect ratios of 15:1 and 20:1, non-surface treated calcium metasilicate microfibers (Nyad G Wollastonite) with an aspect ratio of 20:1, and anhydrous calcium sulfate microfibers with an aspect ratio of 30:1 (Franklin Fiber) were compared to conventional calcium carbonate particulate fillers such as Albaglass Rhombe form having an average particle size of about 0.5 to 1 microns "$\mu m$" and Albocar 5970 Steller form having 1.9 $\mu m$ average particle size, available from Pfizer Minerals, Pigments and Metals Division, Adams, Mass. Both conventional calcium carbonate particulate fillers had an aspect ratio considerably less than 5:1.

To 200 gm aliquots of Resin A was added varying amounts of the aforementioned fillers. The fillers were dried, if necessary, to ensure the moisture content was less than about 0.1 percent. Each resin/filler suspension was mixed using a laboratory dispersator and then rolled to ensure uniformity. Viscosity measurements of each suspension were obtained as previously described. The suspensions were maintained at 23° C. prior to and during the measurement period. For suspensions having a viscosity in excess of 100 Pa s it was necessary to substitute spindle number 7 in place of spindle number 6 as described in Example 1. Table 3a illustrates the viscosity results (in Pa s) for these fillers at varying filler concentration.

TABLE 3a

| Filler conc. (wt. %) | Nyad G treated 20:1 | Nyad G untreated 20:1 | Nyad G Rimm 15:1 | CaSO$_4$ 30:1 | CaCO$_3$—R 1:1 | CaCO$_3$—S 1:1 |
|---|---|---|---|---|---|---|
| 0 | 30 | 30 | 30 | 30 | 30 | 30 |
| 3 | 29 | 39 | 39 | 40 | 37.5 | 38 |
| 7 | 35 | 41.5 | 42 | 52 | 58 | 53 |
| 11 | 37 | 47 | 48 | 65 | 110 | 114 |
| 15 | 44.5 | 54 | 53.5 | — | 248 | 228 |
| 20 | 50 | — | — | — | — | — |
| 25 | 61 | — | — | — | — | — |

As the above data illustrates, the incorporation of microfiber fillers allows substantially greater filler loadings without a resultant detrimental increase in suspension viscosity. For example, the incorporation of twenty percent Nyad G (treated, 20:1 aspect ratio) results in a lower viscosity suspension than the incorporation of only seven percent of a conventional particulate filler.

Example 4
Effect of Microfiber Fillers on Ring Strength and Delamination Several casting tapes were prepared using a resin which incorporates the microfiber fillers of the present invention. To Resin A, of Example 1, was added 15 percent by weight Nyad G 10012 microfiber filler. Four casting tapes were then prepared using a Sontara 8043 hydroentangled apertured non-woven (available from DuPont) having 3.1 fiber bundles per cm in the machine direction, 3.2 fiber bundles per cm in the cross direction, and a mesh size of approximately 9.9 openings per square cm as a backing. Runs 1 and 3 were prepared as controls using unfilled Resin A (i.e., without Nyad G filler). As a means of making a meaningful direct comparison, runs 1 and 2 were prepared using similar resin coating weights (i.e., the weight of resin per unit weight of backing) of 3.5 and 3.65 respectively, while runs 3 and 4 each had resin coating weights of 4.0.

Ring delamination was measured as described in the following procedure. A cylindrical ring comprising 6 layers of the resin-coated material was formed by taking a roll of the resin-coated material from its storage pouch and immersing the roll completely in deionized water having a temperature of about 27° C. for about 30 seconds. The width of the ring formed was the same as the width of the resin-coated material employed, namely, 7.62 cm. The roll of resin-coated material was then removed from the water and the material was wrapped around a 5.08 cm diameter mandrel covered with a thin stockinet (such as 3M Synthetic Stockinet MS02) to form 6 complete uniform layers using a controlled wrapping tension of about 45 grams per centimeter width of material. A free tail of about 15.24 cm was kept and the balance of the roll was cut off. Each cylinder was completely wound within 30 seconds after its removal from the water.

After 15 to 20 minutes from the initial immersion in water, the cured cylinder was removed from the mandrel, and after 30 minutes from the initial immersion in water its delamination strength was determined.

A determination of delamination strength was done by placing the free tail of the cylindrical sample in the jaws of the testing machine, namely, an Instron Model 1122 machine, and by placing a spindle through the hollow core of the cylinder so that the cylinder was allowed to rotate freely about the axis of the spindle. The Instron machine was then activated to pull on the free tail of the sample as a speed of about 127 cm/min. The average force required to delaminate the wrapped layers over the first 33 centimeters of the cylinder was then recorded in terms of force per unit width of sample (newtons/cm width). For each material, at least 5 samples were tested, and the average delamination force was then calculated and reported as the "delamination strength."

Ring strength was measured as described in the following procedure. A 6-layered cylinder of cured casting bandage was formed as described hereinabove for the delamination test except excess material was trimmed off to form these cylindrical rings, leaving no tails.

At a point 30 minutes following the initial immersion in water, each cylinder was removed from its respective mandrel and allowed to cure for 24 to 48 hours in a controlled atmosphere of 25° C.±2° C. and 55%±5% relative humidity. Each cylinder was then placed in a fixture in a commercial testing machine, e.g., an Instron instrument, and compression loads were applied to the cylindrical ring sample along its exterior and parallel to its axis. The cylindrical ring was placed lengthwise between the two bottom bars of the fixture (the bars being 1.9 cm wide, 1.3 cm in height, and 15.2 cm long), with the bars spaced about 4 cm apart. The inside edges of the bars were machined to form a curved surface having a 0.31 cm radius. A third bar (0.63 cm wide, 2.5 cm high, and 15.2 cm long) was then centered over the top of the cylinder, also parallel to its axis. The bottom or contacting edge of the third bar was machined to form a curved surface having a 0.31 cm radius. The third bar was brought down to bear against and crush the cylinder at a speed of about 5 cm/min. The maximum of peak force which was applied while crushing the cylinder was then recorded as the "ring strength," which in this particular instance is the "dry strength" (expressed in terms of force per unit length of the cylinder, i.e., newtons/cm). For each material, at least 5 samples were tested, and the average peak force applied was then calculated and reported as the dry "ring strength."

If better ring strength is observed when performing this ring strength test for the resin coated materials comprising microfiber fillers in accordance with the disclosure herein over resin-coated materials made from the same scrim material and same resin coating weight only without microfiber fillers (i.e., the coatings being compared have the same weight resin per weight of fabric), the microfiber fillers are considered to enhance ring strength and thus be within the scope of the present invention. Likewise, if comparable or better delamination strength is observed when materials containing microfiber fillers are compared against control materials not containing the microfiber fillers, the microfiber fillers are considered to be within the scope of the present invention.

Set out below in Table 4a are the run number, weight percent of Nyad G microfiber in the resin, the total coating weight on the backing, the resin coating weight on the backing, the measured ring strength of the cured structure, and the delamination strength of the cured structure. The sample size for each run in this and the following examples was five unless otherwise noted.

TABLE 4a

| Run # | Weight % Nyad G in Resin A | Coating weight,[1] (gm/gm fabric) | Resin weight, (gm/gm fabric) | Ring strength,[2] (N/cm width) | Ring delamination, (N/cm width) |
|---|---|---|---|---|---|
| 1 | 0 | 3.5 | 3.5 | 71.4 | 4.68 |
| 2 | 15 | 4.3 | 3.65 | 93.5 | 6.08 |
| 3 | 0 | 4.0 | 4.0 | 91.2 | 6.62 |
| 4 | 15 | 4.7 | 4.0 | 102.6 | 8.76 |

[1]By "coating weight" is meant the total weight of the resin and filler per unit weight of fabric.
[2]Measured dry - 24 hours after curing.

As the above data illustrates, the incorporation of microfiber filler adds tremendously to the strength of the composite tape while also contributing to layer-to-layer lamination strength. For purposes of comparison it should be noted that typical fiberglass casting tapes have dry ring strengths of about 95 to 107 N/cm width and ring delamination values of about 7.7 to 10.7 N/cm width. Run number 4 (which incorporates microfiber filler) meets these criteria. Notably, a comparison of run 2 and run 3 indicate that comparable casting tapes can be fabricated when the microfiber fillers of the present invention are substituted for some of the untilled resin.

Thus, one can fabricate a casting tape using less resin than was previously required while maintaining ring strength and ring delamination values. This has important cost benefits (the fillers being less expensive than the resin) as well as providing casting tapes which exhibit a lower exotherm upon curing. This latter feature should decrease any patient discomfort that may result from excess internal temperatures of the wrapped casting material.

Example 5

Effect of Microfiber Fillers on Ring Strength and Delamination

Resin A was filled with 15% by weight Nyad G 10012 microfiber filler and coated on a knitted polyester backing as described in Example 4. The knit was a basic 2 bar knit with the weft yarn laid under 4 needles. A Raschelina RB crochet warp type knittng machine (J. B. Muller Co.) which had 6 needles per cm ( 6 gauge) was used. The chain stitch was a 2/150/34 Power Stretch polyester yarn produced by Unifi Co., Greensboro, N.C. This yarn is a two ply yarn where each yarn is composed of 34 filaments and is 150 denier, making the overall yarn 300 denier. The weft in-lay yarn was a microdenier polyester yarn (1/150/200) produced by DuPont and texturized by Unifi Co.

The tape was rolled up off the knitting machine under essentially no tension. The knits were then heat shrunk by passing the fabric around a pair of 15 cm diameter heated (176° C.) calendar rolls at a speed of 6.1 meters per minute with the rolls held apart. The tapes were then passed through a heated calendar in a nip position to "iron" the fabric flat and to decrease the thickness. The knit produced in this manner had the following properties:

TABLE 5a

| Property | Value |
|---|---|
| Stitches per inch on machine | 5.0 |
| Stitches per inch relaxed | 5.8 |
| Width - working | 100 mm |
| Relaxed width before winder | 100 mm |
| Finished Heat Set: | |
| Width | 100 mm |
| Stitch density per inch | 10 |
| Useable % stretch | 65 |
| Thickness before calendar | 0.045 inch |
| Thickness after calendar | 0.039 inch |

The thickness was measured using an Ames Model 2 thickness gauge (Ames Gauge Co., Waltham, Mass.) equipped with a 2.5 cm diameter contact comparator, by placing the foot down gently onto the fabric. The heated calendar significantly reduced the tape thickness.

The knit was coated at a weight of 3.5 gm filled resin per one gm fabric. The dry ring strength at 24 hours was 187 N/cm width and the ring delamination value was 8.8 N/cm width. This is a substantial improvement over unfilled casting tapes using the same backing.

Example 6

Fiberglass Casting Tape Coated with Microfiber Filled TEOS Resins

To the tetraethylorthosilicate resin described in Example 2 ("Resin T") was added varying amounts of Nyad G microfiber filler. The resins were then coated onto 7.6 cm width Scotchcast TM 2 fiberglass backing at various coating weights. The coating weights were designed to produce casting ropes that had approximately equivalent "resin" coating weight (i.e., the resin weight, without considering the filler contribution, to fabric weight is roughly equivalent). Set out below in Table 6a are the run number, weight percent of Nyad G microfiber in the resin, the total coating weight on the backing, the resin coating weight on the backing, and the measured ring strength of the cured structure. The sample size for each run in this and the following examples was five unless otherwise noted.

TABLE 6a

| Run # | Weight % Nyad G in Resin T | Coating weight, (weight %) | Resin weight, (weight %) | Ring strength,[1] (N/cm width) |
|---|---|---|---|---|
| 1 | 0 | 42.8 | 42.8 | 71.6 |
| 2 | 5 | 44.9 | 42.7 | 82.8 |
| 3 | 10 | 47.6 | 42.8 | 72.7[2] |
| 4 | 15 | 51.2 | 43.5 | 93.2 |

[1]Measured dry - 24 hours after curing.
[2]The value observed for this run is believed to be an anomaly resulting from incorrect coating weight.

As indicated by the above data, the ring strength of a casting tape can be substantially increased by incorporating even small amounts of the microfiber fillers of the present invention. Notably, the tapes containing microfiber fillers still exhibit good drapability and handling characteristics. The microfiber fillers do not appear to adversely affect these properties due to their negligible impact on uncured resin viscosity.

Example 7

Effect of Microfiber Fillers on Set Time

Resin A, from Example 1, was filled with 15 percent Nyad G Wollastokup 10012 as previously described and then coated on the hydroentangled non-woven backing described in Example 4. The resulting composite tape set much faster than expected—therefore the MEMPE catalyst level was reduced. For each run the coating weight was approximately 4.5 gm filled resin per gm fabric. Set out below in Table 7a are the run number, weight percent MEMPE catalyst, and measured set time.

TABLE 7a

| Run # | Weight % MEMPE in Resin A | Coating weight, (gm/gm fabric) | Set Time, (sec) |
|---|---|---|---|
| 1 | 1.25 | 4.5 | 135 |
| 2 | 1.15 | 4.5 | 165 |
| 3 | 1.00 | 4.5 | 180 |
| 4 | 0.80 | 4.5 | 200 |

A target set time of 180 seconds is desirable, therefore, the tape of run 3 was tested for physical properties. The 24 hour ring strength value for this composition was 121 N/cm width. The lamination strength of this composition was so good that a delamination strength could not be determined accurately because the tape ripped. Generally this corresponds to a value in excess of 17.5 N/cm width. Qualitatively the compositions containing microfiber filled resins had exceptional early strength which was not seen with the unfilled resins used previously. The microfiber filled resins also appeared to have noticeably lower peak temperature during the cure exotherm.

Example 8

Orthopedic Casting Tape with a Knit Backing

A knitted backing suitable for use in orthopedic casting was produced using the following components:

TABLE 8a

| Composition | Component of Fabric |
|---|---|
| Front bar: polyester 1/150/68 heat shrink yarn (Dalton Textiles, Oakbrook, Il.) | Chain |
| Back bar: spun polyester 18/2 microdenier yarn (Dalton Textiles, Oakbrook, Il.) | Weft in-lay |
| Middle bar: 180 denier nylon monofilament (Shakespear SN-40-1; Shakespear Monofilament, Columbia, SC.) | Weft insertion |

The knit was constructed using a total of 6 needles in a metric 6 gauge needle bed on a Rashelina RB crochet type warp knitting machine from the J. Muller of America, Inc. The basic knit construction was made with the chain on the front bar and the weft in-lay under 3 needles on the back bar. The middle bar was used to inlay a total of 10 monofilament weft insertion yarns each passing over 7 needles. The weft insertion yarns were mutually interlocked across the bandage width being alternatively laid around one common needle, e.g., weft insertion yarn No. 1 was laid around needles No. 1 and 7, weft insertion yarn No. 2 around needles No. 7 and 13, etc.

The fabric made from this presently particularly preferred composition was heat shrunk by passing the fabric under a forced hot air gun set to a temperature of 150° C. The heat caused the fabric to shrink as the web was wound up on the core under essentially no tension. The fabric was then heated in loose roll form at 175° C. for 20 minutes to anneal the monofilament yarn in the shrunk condition. After cooling, the fabric was passed through a heated calendar roll (79° C.) to bring the fabric thickness down to about 0.97 mm to 1.02 mm. Processed in this way, i.e., with full heat shrinkage followed by calendaring, a fabric with the following properties was produced:

TABLE 8b

| Property | Measured Value |
|---|---|
| Width | 9.5 cm |
| Basis weight | 150 g/cm$^2$ |
| Thickness | 0.97 to 1.02 mm |
| Stitches per cm | 9 |
| Wales per cm | 16 |
| Openings per square cm | 144 |
| Extensibility[1] | 46.3% in the machine direction |
| Extensibility[2] | 63.4% in the cross direction |

[1]Machine direction extensibility was measured at a load of 2.5 Newtons per cm width.
[2]Crosswise direction extensibility was measured at a load of 2.63 Newtons per cm width.

One can determine the degree of extensibility a fabric or casting bandage possess using either an Instron test or a dead weight test on a "stretch table" as described below. A stretch table is constructed by having a pair of 15.25 cm wide clamps spaced exactly 25.4 cm apart. One clamp is stationary and the second clamp is movable on essentially frictionless linear roller bearings. Attached to the movable clamp is a cord secured to an appropriate weight. A stationary board is positioned on the base of the table with a measuring tape to indicate the lineal extension of the fabric when stretched in response to the gravitational force of the applied weight.

Alternatively, an Instron model 1122 machine is set up with fabric clamps spaced exactly 25.4 cm apart. A fabric is placed in the fixtures and tested as indicated herein.

Tests are carried out at ambient temperature (e.g. 23°–25° C.) and at 50% relative humidity. The extensibility test is applicable to both resin coated and uncoated fabrics. Step 1: A piece of unstretched fabric is cut to approximately 30.5 cm. Markings are made on the fabric exactly 25.4 cm apart. If the fabric is coated with a curable resin this operation should be done in an inert atmosphere and the samples sealed until tested. For all samples it is necessary to take extreme care not to stretch the samples prior to testing. Step 2: The fabric is then secured in the test fixture under a very slight amount of tension (e.g. 0.0001 N/cm of bandage width) to ensure that the fabric is essentially wrinkle free. The length of the unstretched bandage should be 25.4 cm since the clamps are separated by this distance. If the 25.4 cm markings applied in the first step do not line up exactly with the clamp the fabric may have been stretched and should be discarded. In the case of a vertical test set up where the weight of the bandage (especially if resin coated) is sufficient to result in extension of the fabric the bandage should be secured in the clamps at exactly the marks made in step 1. Step 3: A weight is then attached to the clamp. Unless otherwise indicated, the weight should be 268 g/cm width of tape. Step 4: The sample is then extended by slowly and gently extending the fabric until the full weight is released. In cases where an Instron is used the sample is extended at a rate of 12.7 cm/min until the proper load has been reached. If the fabric being tested continues to stretch under the applied load the % stretch is taken 1 min after applying the load. Step 5: The % stretch is recorded as the amount of lineal extension divided by the original sample length and this value multiplied by 100. Note that testing of moisture curable resin coated fabrics must be performed rapidly in order to avoid having cure of the resin effect the results.

The fabric described above was coated with the following resin composition. A 3.8 liter (one gallon) glass vessel equipped with a 12.7 cm×2.54 cm×0.318 cm Teflon ™ impeller, addition funnel, nitrogen purge line, and thermometer was assembled and purged with nitrogen for 30 minutes to ensure that the entire apparatus was completely dry. The following chemicals were added to the reactor through the addition funnel in order and at 5 minute intervals:

TABLE 8c

| Chemical | Equivalent weight[3] | Weight (%) |
|---|---|---|
| Isonate 2143L (Dow Chemical Co.) | 144.3 | 56.8 |
| p-toluenesulfonyl chloride | | 0.05 |
| Antifoam 1400 (Dow Chemical) | | 0.18 |
| Butylated hydroxytoluene ("BHT") | | 0.48 |
| MEMPE[1] | | 1.15 |
| Pluronic F-108 (BASF) | 7250 | 5.00 |
| Arcol PPG-2025 (Arco) | 1016.7 | 22.2 |
| Niax E-562[2] | 1781 | 8.50 |
| Arcol LG-650 (Arco) | 86.1 | 5.60 |

[1]"MEMPE" = Morpholinoethylmorpholinoisopropyl ether.
[2]"E-562" = Polymer filled polyol (formerly available from the Union Carbide Corp. and now available from Arco as Arcol Polyol 24-32).
[3]The combined ingredients provide an NCO to OH ratio of 4.24 and an NCO equivalent weight of 323.3 g/equivalent.

The agitation rate was gradually increased as the viscosity increased. The vessel was temporarily insulated with glass wool, gently heated with a heating mantle, and the temperature of the reaction was allowed to increase to 65°–71° C. and held at that temperature for 1.5 hours. The glass wool was removed along with the agitator, thermometer, and addition funnel. The vessel was sealed and the resin was allowed to cool for 24 hours.

After this time, 20 parts Nyad G Wollastokup 10012 (available from Nyco, Willsboro, N.Y.) microfiber filler was added to 80 parts resin to yield a composition having 20% by weight microfiber filler. The resin was sealed inside a jar and allowed to cool overnight while rotating on a roller at about 7 revolutions per minute (rpm). This filled resin composition was then coated on the above described fabric at a coating weight of 3.5 grams filled resin per 1 gram fabric (i.e., approximately 2.8 grams resin, on a filler free basis, per gram fabric). The coating was perforated by spreading the resin directly on one surface and while the fabric was under minimal tension. The coated fabric was then converted into 3.35 m rolls wrapped around a 1.2 cm diameter polyethylene core. The converting operation was also done under minimal tension to avoid stretching the fabric. The rolls were then placed into aluminum foil laminate pouches for later evaluation.

The material was evaluated by: (1) removing the roll from the pouch; (2) dipping the roll under 23°–25° C. water while squeezing three times, followed by a final squeeze to remove excess water; and (3) wrapping the bandage on a forearm. The material was found to be very conformable and easy to work with without wrinkling. The material was also found to be much more palpable than typical fiberglass casting tapes. The cast quickly became very strong (i.e., within 20–30 minutes) and had a very pleasing appearance.

Example 9

Ring Stiffness of Microfiber Filled Resin Casting Tapes

The stiffness of casting tapes may be quantified by the slope of the compression stress (force applied) vs. strain (deformation) curve obtained during the testing of dry ring strength. This slope is referred to herein as the "ring stiffness" of the material.

A fabric was knit according to Example 5 except that a 180 denier nylon monofilament SN-40-1 (available from Shakespear Monofilament, Columbia, S.C.) was used as a weft in-lay. Each of three monofilament yarns were laid across 21 needles in a substantially nonoverlapping configuration to completely fill the width of the fabric (note that two adjacent monofilaments do not overlap each other but are being alternatively laid around one common needle).

The fabric made from this presently particularly preferred composition was heat shrunk by passing the fabric under a forced hot air gun set to a temperature of 150° C. The heat caused the fabric to shrink as the web was wound up on the core under essentially no tension. The fabric was then heated in loose roll form at 175° C. for 20 minutes to anneal the monofilament yarn in the shrunk condition. After cooling, the fabric was passed through a heated calendar roll (79° C.) to bring the fabric thickness down to about 0.12 cm. Processed in this way, i.e., with full heat shrinkage followed by calendaring, a fabric with the following properties was produced:

TABLE 9a

| Property | Measured Value |
| --- | --- |
| Width | 8.9 cm |
| Thickness | 0.12 cm |
| Extensibility[1] | 45% in the machine direction |

[1]Machine direction extensibility was measured at a load of 2.63 Newtons per cm width.

The fabric described above was coated with the following resin composition. A 3.8 liter (one gallon) glass vessel equipped with a 12.7 cm×2.54 cm×0.318 cm Teflon TM impeller, addition funnel, nitrogen purge line, and thermometer was assembled and purged with nitrogen for 30 minutes to ensure that the entire apparatus was completely dry. The following chemicals were added to the reactor through the addition funnel in order and at 5 minute intervals:

TABLE 9b

| Chemical | Equivalent weight[3] | Weight (%) |
| --- | --- | --- |
| Isonate 2143L (Dow Chemical Co.) | 144.3 | 56.8 |
| p-toluenesulfonyl chloride | | 0.05 |
| Antifoam 1400 (Dow Chemical) | | 0.18 |
| Butylated hydroxytoluene ("BHT") | | 0.48 |
| MEMPE[1] | | 1.15 |
| Pluronic F-108 (BASF) | 7250 | 5.00 |
| Arcol PPG-2025 (Arco) | 1016.7 | 22.2 |
| Niax E-562[2] | 1781 | 8.50 |
| Arcol LG-650 (Arco) | 86.1 | 5.60 |

[1]"MEMPE" = Morpholinoethylmorpholinoisopropyl ether.
[2]"E-562" = Polymer filled polyol (formerly available from the Union Carbide Corp. and now available from Arco as Arcol Polyol 24-32).
[3]The combined ingredients provide an NCO to OH ratio of 4.24 and an NCO equivalent weight of 323.3 g/equivalent.

The agitation rate was gradually increased as the viscosity increased. The vessel was temporarily insulated with glass wool, gently heated with a heating mantle, and the temperature of the reaction was allowed to increase to 65°–71° C. and held at that temperature for 1.5 hours. The glass wool was removed along with the agitator, thermometer, and addition funnel. The vessel was sealed and the resin was allowed to cool for 24 hours.

Two separate batches of resin/microfiber suspension were prepared. To prepare the first suspension ("#9-20"), 20 parts Nyad G Wollastokup 10012 (available from Nyco, Willsboro, N.Y.) microfiber filler was added to 80 parts resin to yield a composition having 20% by weight microfiber filler. To prepare the second suspension ("#9-25"), 25 pans Nyad G Wollastokup 10012 (available from Nyco, Willsboro, N.Y.) microfiber filler was added to 75 parts resin to yield a composition having 25% by weight microfiber filler. The suspensions were sealed inside a jar and allowed to cool overnight while rotating on a roller at about 7 revolutions per minute (rpm).

These filled resin compositions were then separately coated on the above described fabric at a coating weight of 3.8–4.0 grams filled resin per 1 gram fabric. The coating was performed by spreading the resin directly on one surface and while the fabric was under minimal tension. The coated fabric was then convened into 3.35 m rolls wrapped around a 1.2 cm diameter polyethylene core. The converting operation was also done under minimal tension to avoid stretching the fabric. The rolls were then placed into aluminum foil laminate pouches for later evaluation.

The materials were tested according to the dry ring strength test as previously discussed and were found to have the following properties. In addition, two commercially available fiberglass casting materials were tested for comparison.

TABLE 9c

| Sample | Filler content (%) | Coating weight, (g/g fabric) | Ring strength, (N/cm width) | Ring stiffness, (N/cm width) |
| --- | --- | --- | --- | --- |
| #9-20 | 20 | 4.0 | 140 | 2320 |
| #9-25 | 25 | 3.8 | 160 | 2890 |
| Scotchcast TM Plus Casting Tape | | | 88.3 | 2570 |
| Dynacast TM Extra | | | 100.7 | 1950 |

As the above data illustrates the non-fiberglass tapes containing the microfiber filler have comparable ring stiffness to commercially available fiberglass casting tapes.

Various modifications and alterations of this invention will be apparent to those skilled in the art without departing from the scope and spirit of this invention, and it should be understood that this invention is not limited to the illustrative embodiments set forth herein.

What is claimed is:

1. An article, comprising:
   a fabric sheet;
   a curable liquid resin coated onto said fabric sheet; and
   a microfiber filler, having an aspect ratio at least 5:1, associated with said resin.

2. An article, as defined in claim 1, wherein said fabric sheet comprises fiberglass fibers.

3. An article, as defined in claim 1, wherein said fabric sheet comprises organic fibers.

4. An article, as defined in claim 1, wherein said curable resin is a water-curable resin comprising isocyanate-functional prepolymers.

5. An article, as defined in claim 1, wherein said curable resin is a water-curable resin comprising a water-reactive liquid organometallic compound and an organic polymer.

6. An article, as defined in claim 1, wherein said microfiber is characterized as having an aspect ratio between 5:1 and 200:1.

7. An article, as defined in claim 4, wherein said microfiber is characterized as having an aspect ratio between 5:1 and 50:1.

8. An article, as defined in claim 3, wherein said microfiber is characterized as having an aspect ratio between 10:1 and 30:1.

9. An article, as defined in claim 6, wherein said microfiber is characterized as having a mean diameter between approximately 1 and 60 microns and a mean length between approximately 25 and 1000 microns.

10. An article, as defined in claim 7, wherein said microfiber is characterized as having a mean diameter between approximately 1 and 40 microns and a mean length between approximately 30 and 1,000 microns.

11. An article, as defined in claim 7, wherein said microfiber is characterized as having a mean diameter between approximately 1 and 30 microns and a mean length between approximately 30 and 500 microns.

12. An article, as defined in claim 1, wherein said microfiber is selected from the group consisting of carbon/graphite fibers, aramid fibers, boron fibers, potassium titanate fibers, calcium sulfate fibers, asbestos, and calcium metasilicate.

13. An article, as defined in claim 6, wherein said microfiber comprises calcium sulfate fibers.

14. An article, as defined in claim 6, wherein said microfiber comprises calcium metasilicate.

15. An article, as defined in claim 1, wherein said microfiber is present in an amount in said resin between about 3 and about 25 percent microfiber based on the weight of resin and microfiber filler and exclusive of the weight of the fabric.

16. An article, as defined in claim 1, wherein said microfiber is present in an amount in said resin between about 7 and about 25 percent microfiber based on the weight of resin and microfiber filler and exclusive of the weight of the fabric.

17. An article, as defined in claim 1, wherein said microfiber and said resin are in the form of a suspension prior to application to said fabric, and wherein said suspension has a viscosity between about 5 and 100 Pa s.

18. An article, as defined in claim 1, wherein said microfiber and said resin are in the form of a suspension prior to application to said fabric, and wherein said suspension has a viscosity between about 10 and 70 Pa s.

19. An article, as defined in claim 1, wherein said fabric sheet comprises organic fibers, wherein said microfiber filler is selected from the group consisting of calcium sulfate fibers and calcium metasilicate fibers, wherein said microfiber is characterized as having an aspect ratio between 5:1 and 50:1 and is present in an amount in said resin between about 7 and about 25 percent microfiber based on the weight of resin and microfiber and exclusive of the weight of the fabric.

20. A method of making an orthopedic casting bandage, comprising the step of:
    coating a fabric with a curable liquid resin and a microfiber filler.

21. A method according to claim 20, wherein said resin and microfiber filler are concurrently coated onto said fabric.

22. A method according to claim 20, wherein said fabric comprises fiberglass fibers.

23. A method according to claim 20, wherein said fabric comprises organic fibers.

24. A method according to claim 20, wherein said curable resin is a water-curable resin comprising isocyanate-functional prepolymers.

25. A method according to claim 20, wherein said curable resin is a water-curable resin comprising a water-reactive liquid organometallic compound and an organic polymer.

26. A method according to claim 20, wherein said microfiber is characterized as having an aspect ratio between 5:1 and 50:1.

27. A method according to claim 23, wherein said micro fiber is characterized as having an aspect ratio between 10:1 and 30:1.

28. A method according to claim 26, wherein said microfiber is characterized as having a mean diameter between approximately 1 and 60 microns and a mean length between approximately 25 and 1000 microns.

29. A method according to claim 27, wherein said microfiber is characterized as having a mean diameter between approximately 1 and 40 microns and a mean length between approximately 30 and 1,000 microns.

30. A method according to claim 20, wherein said microfiber is selected from the group consisting of carbon/graphite fibers, aramid fibers, boron fibers, potassium titanate fibers, calcium sulfate fibers, asbestos, and calcium metasilicate.

31. A method according to claim 20, wherein said microfiber is present in an amount in said resin between about 7 and about 25 percent microfiber based on the weight of resin and microfiber filler and exclusive of the weight of the fabric.

32. A method according to claim 20, wherein said microfiber and said resin are in the form of a suspension prior to application to said fabric, and wherein said suspension has a viscosity between about 5 and 100 Pa s.

33. A method according to claim 20, wherein said microfiber and said resin are in the form of a suspension prior to application to said fabric, and wherein said suspension has a viscosity between about 10 and 70 Pa s.

34. A method of applying an orthopedic casting material comprising the steps of:
    contacting a casting material comprising a fabric sheet, a water-curable liquid resin, and microfiber fillers with water to initiate curing of said resin, and applying said casting material to a patient.

35. A method according to claim 34, wherein said microfiber fillers are selected from the group consisting of calcium sulfate fibers, and calcium metasilicate; said microfiber and said resin being in the form of a suspension prior to application to said fabric, and wherein said suspension has a viscosity between about 5 and 100 Pa s; and said microfiber fillers are characterized as having an aspect ratio between 5:1 and 50:1.

* * * * *

UNITED STATES PATENT AND TRADEMARK OFFICE
CERTIFICATE OF CORRECTION

PATENT NO. : 5,354,259

DATED : October 11, 1994

INVENTOR(S) : Matthew T. Scholz and Worku A. Mindaye

It is certified that error appears in the above-identified patent and that said Letters Patent is hereby corrected as shown below:

Col. 2, line 2, "east" should read -- cast --.

Col. 2, line 41, "an" should read -- art --

Col. 2, line 66, "08/008,761" should read -- 08/008,161 --.

Col. 5, line 49, "an" should read -- art --.

Col. 6, lines 60-61, "Coming" should read -- Corning --.

Col. 6, line 62, "Coming" should read -- Corning --.

Col. 10, line 43, "untilled" should read -- unfilled --.

Col. 15, line 68, "untilled" should read -- unfilled --.

Col. 16, line 22, "yam" should read -- yarn --.

Col. 20, line 17, "perforated" should read -- performed --.

UNITED STATES PATENT AND TRADEMARK OFFICE
CERTIFICATE OF CORRECTION

PATENT NO. : 5,354,259

DATED : October 11, 1994

INVENTOR(S) : Matthew T. Scholz and Worku A. Mindaye

It is certified that error appears in the above-indentified patent and that said Letters Patent is hereby corrected as shown below:

Col. 20, line 49, "yams" should read -- yarns --.

Col. 21, line 61, "convened" should read -- converted --.

Signed and Sealed this

Twenty-third Day of January, 1996

Attest:

BRUCE LEHMAN

*Attesting Officer*     *Commissioner of Patents and Trademarks*